(12) United States Patent
Bazan et al.

(10) Patent No.: US 8,044,225 B1
(45) Date of Patent: Oct. 25, 2011

(54) ZWITTERIONIC GROUP VIII TRANSITION METAL INITIATORS SUPPORTED BY OLEFIN LIGANDS

(75) Inventors: Guillermo C. Bazan, Goleta, CA (US); Yaofeng Chen, Shanghai (CN)

(73) Assignee: The Regents of the University of California, Oakland, CA (US)

( * ) Notice: Subject to any disclaimer, the term of this patent is extended or adjusted under 35 U.S.C. 154(b) by 1443 days.

(21) Appl. No.: 11/519,618

(22) Filed: Sep. 12, 2006

(51) Int. Cl.
*C07F 15/00* (2006.01)
*C07F 15/04* (2006.01)
*C08F 4/80* (2006.01)
*B01J 31/22* (2006.01)

(52) U.S. Cl. ............ 556/140; 556/7; 556/32; 526/134; 526/160; 526/164; 526/171; 526/172; 502/152; 502/155

(58) Field of Classification Search .................. 556/140, 556/7, 32; 526/134, 171, 172, 160, 164; 502/152, 155
See application file for complete search history.

(56) References Cited

U.S. PATENT DOCUMENTS 7,776,943 B2 * 8/2010 Scott et al. .................... 523/351

OTHER PUBLICATIONS

Ittel, S. D.; Johnson, L. K.; Brookhart, M. *Chem. Rev.* 2000, 100, 1169-1203.
Gibson, V. C.; Spitzmesser, S. K. *Chem. Rev.* 2003, 103, 283-315.
Johnson, L. K.; Killian, C. M.; Brookhart, M. *J. Am. Chem. Soc.* 1995, 117, 6414-6415.
Klabunde, U.; Ittel, S. D. *J. Mol. Catal.* 1987, 41, 123-124.
Ostoja-Starzewski, K. A.; Witte, J.; Reichert, K. H.; Vasiliou, G. In *Transition Metals and Organometallics as Catalysts for Olefin Polymerization*; Kaminsky, W., Sinn, H., Eds.; Springer: Berlin, 1998; p. 349.
Younkin, T. R.; Connor. E. F.; Henderson, J. I.; Friedrich, S. K.; Grubbs, R. H.; Bansleben, D. A. *Science* 2000, 287, 460-462.
Jenkins, J. C.; Brookhart, M. *J. Am. Chem. Soc.* 2004, 126, 5827-5842.
Strauch, J. W.; Erker, G.; Kehr, G.; Fröhlich, R. *Angew. Chem. Int. Ed. Engl.* 2002, 41, 2543-2546 Bazan, G. C.; Rodriguez, G.; Ashe III, A. J.; Al-Ahmad, S.; Müller, C. *J. Am. Chem. Soc.* 1996, 118, 2291-2292.
Barnhart, R. W.; Bazan, G. C.; Mourey, T. *J. Am. Chem. Soc.* 1998, 120, 1082-1083.
Komon, Z. J. A.; Diamond, G. M.; Leclerc, M. K.; Murphy, V.; Okazaki, M.; Bazan, G. C. *J. Am. Chem. Soc.* 2002, 122, 15280-15285.
Wasilke, J. C.; Obrey, S. J.; Baker, R. T.; Bazan, G. C. *Chem. Rev.* 2005, 105, 1001-1020.
Bonnet, M. C.; Dahan, F.; Ecke, A.; Keim, W.; Schultz, R. P.; Tkatchenko, I. *J. Chem. Soc., Chem. Commun.* 1994, 615-616.
Komon, Z. J. A.; Bu, X.; Bazan, G. C. *J. Am. Chem. Soc.* 2000, 122, 1830-1831.
Komon, Z. J. A.; Bu, X.; Bazan, G. C. *J. Am. Chem. Soc.* 2000, 122, 12379-12380.
Deng, L. Q.; Margl, P.; Ziegler, T. *J. Am. Chem. Soc.* 1997, 119, 1094-1100.
Lee, B. Y.; Bazan, G. C.; Vela, J.; Komon, Z. J. A.; Bu, X. *J. Am. Chem. Soc.* 2001, 123, 5352-5353.
Chen, Y.; Wu, G.; Bazan, G. C. *Angew, Chem., Int. Ed. Engl.* 2005, 44, 1108-1112.
Kwon, H. Y.; Lee, S. Y.; Lee, B. Y.; Shin, D. M.; Chung, Y. K. *Dalton Transactions* 2004, 921-928.
Shim, C. B; Kim, Y. H.; Lee, B. Y.; Shin, D. M.; Chung, Y. K. *J. Organomet. Chem.* 2003, 675, 72-76.
Kim, Y. H.; Kim, T. H.; Lee, B. Y.; Woodmansee, D.; Bu, X.; Bazan, G. C. *Organometallics* 2002, 21, 3082-3084.
Shim, C. B.; Kim, Y. H.; Lee, B. Y.; Dong, Y.; Yun. H. *Organometallics* 2003, 22, 4272-4280.
Lee, B. Y.; Bu, X., Bazan, G. C. *Organometallics* 2001, 20, 5425-5431.
Schmid, M.; Eberhardt, R.; Kukral, J.; Rieger, B. *Z. Naturfosch. B* 2002, 57, 1141-1146.
Carmona, E.; Paneque, M.; Poveda, M. L *Polyhedron* 1989, 8, 285-291.
Pappalardo, D.; Mazzeo, M.; Antinucci, S.; Pellecchia, C. *Macromolecules* 2000, 33, 9483-9487.
Ewen, J. A. *J. Am. Chem. Soc.* 1984, 106, 6355-6364.

* cited by examiner

*Primary Examiner* — Caixia Lu
(74) *Attorney, Agent, or Firm* — Berliner & Associates

(57) ABSTRACT

A zwitterionic Group VIII transition metal complex containing the simple and relatively small 3-(arylimino)-but-1-en-2-olato ligand that catalyzes the formation of polypropylene and high molecular weight polyethylene. A novel feature of this catalyst is that the active species is stabilized by a chelated olefin adduct. The present invention also provides methods of polymerizing olefin monomers using zwitterionic catalysts, particularly polypropylene and high molecular weight polyethylene.

11 Claims, 2 Drawing Sheets

ZWITTERIONIC GROUP VIII TRANSITION METAL INITIATORS SUPPORTED BY OLEFIN LIGANDS

STATEMENT REGARDING FEDERALLY SPONSORED RESEARCH OR DEVELOPMENT

This invention was made with Government support under Grant No. DE-FG03098ER14910 from the United States Department of Energy. The Government has certain rights in this invention.

FIELD OF THE INVENTION

The invention relates generally to the polymerization of olefin monomers and in particular to polymerization by zwitterionic metal catalysts.

BACKGROUND OF THE INVENTION

Nickel-based olefin oligomerization and polymerization initiators are of interest in industrial and academic laboratories [1,2]. Cationic versions are the most commonly encountered [3]. Neutral species, although less active, are under investigation because of their higher tolerance toward functionalities [4, 5, 6, 7]. Zwitterionic counterparts are the least common and provide an intermediate range of reactivities [8].

While developing tandem catalytic processes [9, 10, 11, 12], one of the inventors discovered that the reactivity of SHOP-type catalysts such as $[(C_6H_5)_2PC_6H_4C(O)O\text{-}\kappa^2P,O]$ $Ni(\eta^3\text{—}CH_2CMeCH_2)$ [13] increases upon addition of $B(C_6F_5)_3$ [14,15]. Carbonyl coordination to the borane gives zwitterionic $[(C_6H_5)_2PC_6H_4C(O\text{—}B(C_6F_5)_3)O\text{-}\eta^2P,O]Ni$ $(\eta^3\text{—}CH_2CMeCH_2)$ and removes electron density from nickel. Examination of ligand/reactivity relationships for cationic Ni(diimine) initiators [3,16] led to the design and synthesis of $\{(H_3C)C[=NAr]C[O\text{—}B(C_6F_5)_3][=NAr]\text{-}\kappa^2N, N''\}Ni(\eta^3\text{—}CH_2C_6H_5)$, with which high molecular weight polyethylene (PE) can be produced for bulky aromatic (Ar) substituents [17]. Several other ligand types have been reported that are amenable to the concept of Lewis acid attachment on a ligand site to redistribute electron density, including 3-(1-arylimino-ethyl)-acetylacetonato [18], 2-diphenylphosphinylbenzamido [19], N-(2-benzoylphenyl) benzamido [20], α-iminoenamido [21], 2-(alkyldeneamino) benzoato [22] and iminoamido pyridine [23]. However, none of these systems has been able to produce high molecular weight PE, in the absence of bulky Ar substituents, or polypropylene.

BRIEF SUMMARY OF THE INVENTION

The present invention provides a zwitterionic Group VIII transition metal complex containing the simple and relatively small 3-(arylimino)-but-1-en-2-olato ligand that initiates the polymerization or co-polymerization of olefins. A novel feature of this catalyst is that the active species is stabilized by a chelated olefin adduct.

The present invention also provides a process of polymerizing olefin monomers using zwitterionic catalysts. In particular, the olefin, preferably a monomer, is selected from the group consisting essentially of: (1) olefins having formula $R^vCH=CH_2$, wherein $R^v$ is hydrogen, a substituted or unsubstituted hydrocarbyl group, or a substituted or unsubstituted hydrocarbyl bearing functional group; (2) a substituted or unsubstituted cyclopentene, (3) a substituted or unsubstituted styrene, (4) a substituted or unsubstituted norbornene derivative bearing functional group, and (5) a polar olefin. Preferred olefins are polypropylene and ethylene for the formation of polypropylene and high density polyethylene.

The zwitterionic Group VIII transition metal complex acts as an initiator in the formation of polymers and co-polymers, but in this specification will be referred to either as an initiator or catalyst.

DETAILED DESCRIPTION OF THE INVENTION

The initiator/catalyst of the present invention is a zwitterionic Ni complex containing a 3-(arylimino)-but-1-en-2-olato ligand stabilized by a chelated olefin adduct. In particular, the present invention provides a catalyst of the following formula 1:

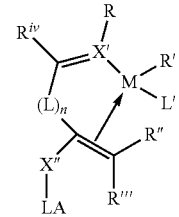

wherein M is a Group VIII transition metal such as Ni, Pd, Pt; R' is a one electron hydrocarbyl, such as methyl, ethyl, substituted or unsubstituted R' is
→ benzyl (which is a combination of a sigma bond and a pi-bond from the bound aromatic unit), and the like;
L' is a two electron ligand, such as a phosphine, amine, olefin, ether, and the like, or is a link to R' when R' is R' is → benzyl;
X' is a two electron donor, such as imine, phosphine, carbonyl, and the like;
each R, R'', R''', $R^{iv}$ is independently hydrogen, an alkyl or a substituted or unsubstituted aryl group;
$(L)_n$ is a tether group, such as a series of methylene carbons, oxygen, amine, and the like, wherein n is 0 or 1;
X'' is a component having two electron donor functionality, such as oxygen, amine, phosphine, and the like;
LA is a Lewis Acid, such as a trisubstituted boron, trisubstituted aluminum or a proton; and
the olefin bearing X'' is bound to the metal center.

In preferred embodiments:
M is nickel;
R' is → benzyl;
L' is linked to R'
X' is an imine;
R is an aryl group;
R'' is an alkyl group;
$R^{iv}$ is an alkyl group;
R''' is hydrogen;
n is 0;
X'' is oxygen; and
LA is a trisubstituted boron.

A particularly preferred catalyst is compound 2 shown in the scheme 1 below, having the structure:

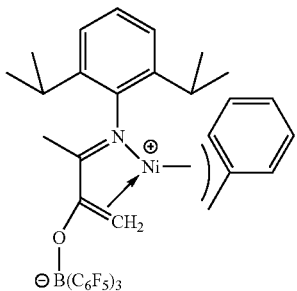

Preparation of the Zwitterionic Ni Complex Catalysts of this Invention is exemplified by the specific reactions shown in Scheme 1:

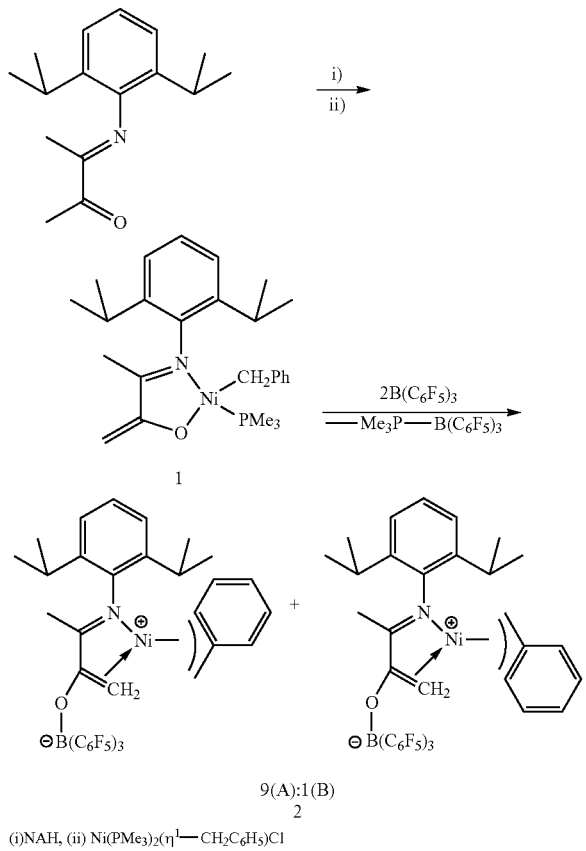

(i) NaH, (ii) Ni(PMe$_3$)$_2$($\eta^1$—CH$_2$C$_6$H$_5$)Cl

Figure 1:
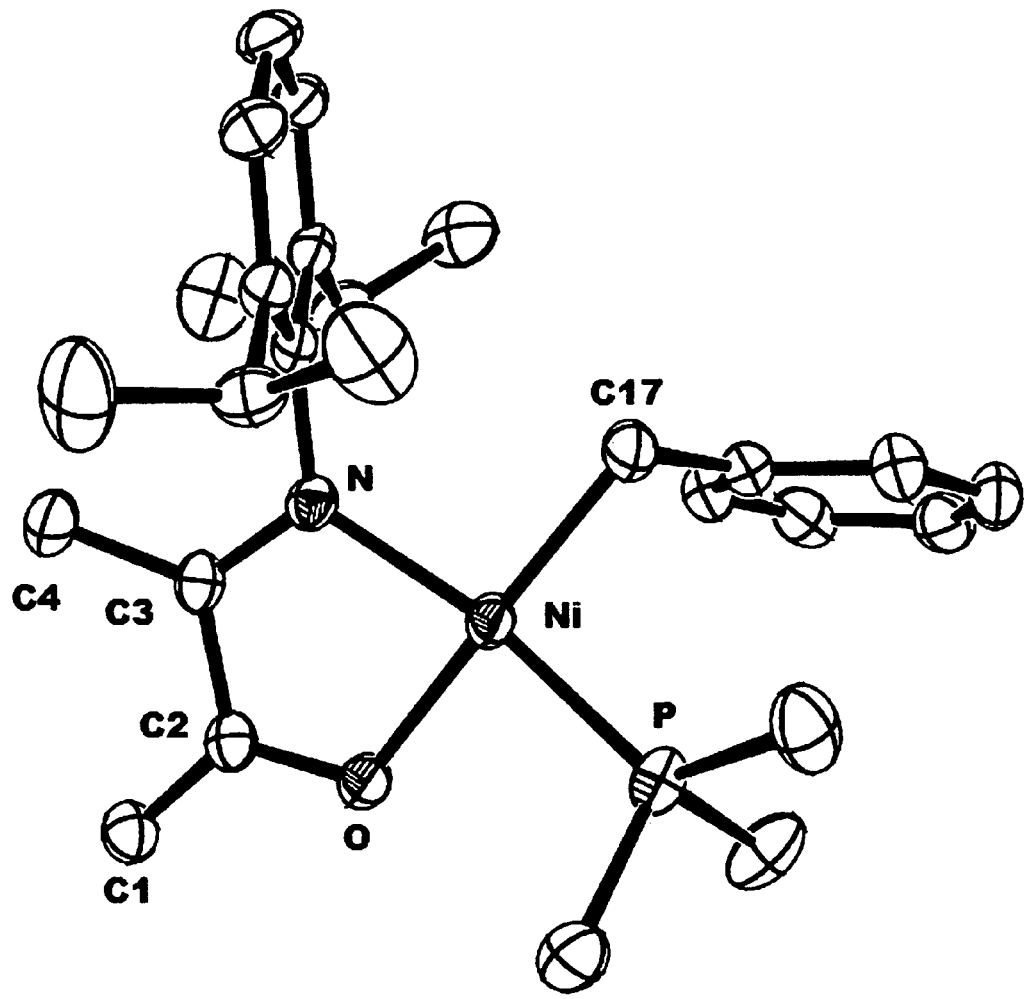
FIG. 1 is an Oak Ridge Thermal Ellipsoid Program (ORTEP) molecular modeling drawing of an intermediate compound in the production of an initiator of this invention, at the 50% probability level, with hydrogen atoms omitted for clarity.

As shown in Scheme 1, synthetic access begins with 3-(2,6-diisopropylphenylimino)-butan-2-one [24], which is obtained by condensation of 2,6-diisopropylaniline with 2,3-butanedione. Deprotonation with NaH in THF provides the sodium salt in 80% yield. Subsequent reaction of the salt with Ni(PMe$_3$)$_2$($\eta^1$—CH$_2$C$_6$H$_6$)Cl [25] provides a new compound, which contains the ligand fragment ($^1$H NMR in C$_6$D$_6$: 4.91, 4.63 ppm), an $\eta^1$-benzyl group ($^1$H NMR: 7.56 ppm) and PMe$_3$. Single crystals of the product were obtained from a solution of pentane and the results are shown in FIG. 1. The product is thus (3-(2,6-diisopropylphenylimino)-but-1-en-2-olato)($\eta^1$-benzyl)-(trimethylphosphine)-nickel (compound 1 as shown in Scheme 1).

Structural characterization of compound 1 reveals a distorted square-planar geometry with a cis relationship between the benzyl ligand and the imine nitrogen. The 3-(2,6-diisopropylphenylimino)-but-1-en-2-olato ligand coordinates to the nickel via the nitrogen and oxygen atoms with Ni—O and Ni—N bond lengths of 1.9031(16) and 1.9555(18) Å, respectively. The C$_1$-C$_2$ (1.344(3) Å) and C3-N (1.294(3) Å) distances are consistent with double bond character, whereas the C$_2$-C$_3$ (1.486(3) Å), C3-C4 (1.497(3) Å) and C2-O (1.315(3) Å) distances reveal single bond character. These data indicate localized bonding in the chelating ring.

The addition of 2 equivalents B(C$_6$F$_5$)$_3$ to compound 1 in toluene results in the formation of Me$_3$P—B(C$_6$F$_5$)$_3$, which precipitates out of solution, and a new organometallic product. $^1$H NMR spectra of the product show the formation of two isomers in a 9:1 ratio. The upfield shift of the aromatic signals from —CH$_2$C$_6$H$_5$ from 6.9 to 7.6 to 5.9 to 6.6 ppm indicates □$^3$-coordination. The vinyl protons are observed as a pair of doublets in the range of 3.25 to 5.02 ppm. The $^{11}$B NMR spectrum shows a signal at −2.6 ppm, consistent with boron-oxygen coordination. $^1$H-NOE spectroscopy between the vinyl group and the benzyl group indicates that the sets of isomers arise from pseudorotamers of the benzyl ligand [23] and that the major isomer contains a cis relationship between the vinyl group and the benzyl group, as shown in Scheme 1.

Figure 2:
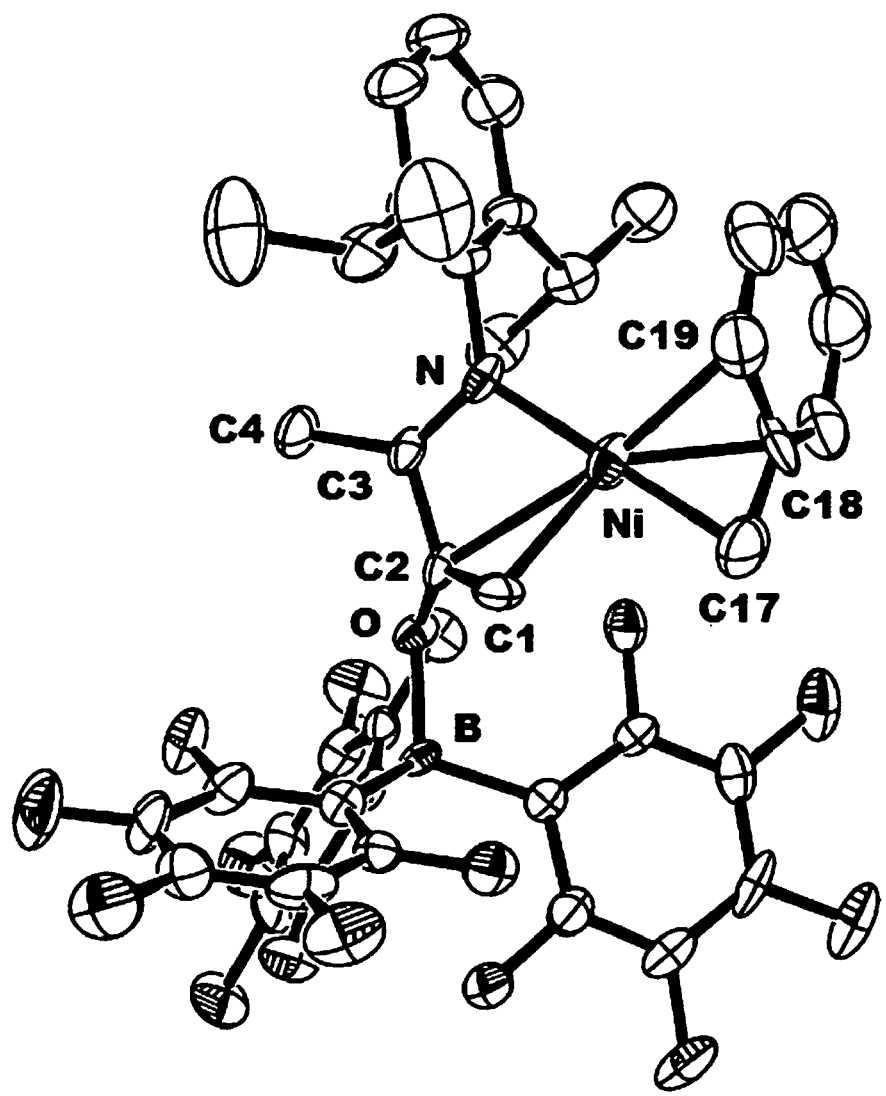
FIG. 2 is an ORTEP molecular modeling drawing of the initiator of this invention, at the 50% probability level, with hydrogen atoms omitted for clarity.

Single crystals of compound 2 formed from a toluene solution and the structure is shown in FIG. 2. Isomer 2(A) was obtained preferentially. The oxygen binds to the Lewis acidic boron and by doing so, forces coordination of the olefin to the nickel center. The distances from Ni to C1 and C2, are 2.109 (6) Å and 2.455(6) Å, respectively. The rotation of the C$_2$-C$_3$ bond and the C$_1$-C$_2$-C$_3$—N torsional angle) (41.6(8)° optimize overlap between the π-orbital of the —C═CH$_2$ group and Ni. The C2-O distance (1.319(6) Å) is characteristic of a single bond, while the C$_1$-C$_2$ (1.371(7) Å) distance is more indicative of a double bond. These observations are consistent with the charge distribution as shown for structures of compound 2(A) and 2(B) in Scheme 1. The C3-N distance (1.300 (6) Å) is close to that observed in compound 1 (1.294(3) Å). The N—Ni bond length (1.900(4) Å) is 0.055 Å is shorter than that of compound 1 (1.9555(18) Å), revealing a more electron deficient metal center in the zwitterionic compound.

The zwitterionic initiators/catalysts enable the polymerization of olefins. In particular, the olefin, preferably a monomer, is selected from the group consisting essentially of: (1) olefins having formula R$^v$CH═CH$_2$, wherein R$^v$ is hydrogen, a substituted or unsubstituted hydrocarbyl group, or a substituted or unsubstituted hydrocarbyl bearing functional group; (2) a substituted or unsubstituted cyclopentene, (3) a substituted or unsubstituted styrene, (4) a substituted or unsubstituted norbornene derivative bearing functional group, and (5) a polar olefin. Preferred olefins are polypropylene and ethylene for the formation of polypropylene and high density polyethylene. The zwitterionic catalysts of this invention catalyze the formation of polypropylene and high molecular weight polyethylene, e.g., having a molecular weight from 50 K to over a million Daltons Examples 1-8

Ethylene polymerization reactions with compound for 2 were studied, and the results of these studies are listed in Table 1.

TABLE 1

Polymerization of ethylene[a] and propylene[b] with compound 1 or 2.

| Example | Compound (μmol) | Additive (equiv.) | T (°C.) | Time (min) | Activity[c] | Mw | PDI | $T_m$ (°C.) |
|---|---|---|---|---|---|---|---|---|
| 1 | 2(6)[a] | 0 | 30 | 10 | 453 | 135 500 | 5.86 | 135 |
| 2 | 2(3)[a] | BCF(6) | 30 | 8 | 2190 | 134 800 | 2.59 | 134 |
| 3 | 2(3)[a] | BCF(6) | 75 | 8 | 4050 | 149 700 | 6.90 | 117 |
| 4 | 2(2)[a] | BCF(6) | 75 | 5 | 6900 | 132 300 | 6.86 | 118 |
| 5 | 1(6)[a] | 0 | 30 | 10 | 0 | | | |
| 6 | 2(20)[b] | BCF(2) | 17 | 90 | 18 | 207 400 | 2.05 | |
| 7 | 2(20)[b] | BCF(3) | 17 | 90 | 34 | 205 800 | 2.07 | 70 |
| 8 | 2(20)[b] | BCF(3) | 17 | 240 | 17 | 242 700 | 2.23 | |

[a]Polymerization conditions: 28 g toluene, 100 psi ethylene.
[b]Polymerization conditions: 20 g toluene, 26 mL propylene.
[c]Activity in kg polymer/(mol cat · h).

Addition of 100 psi ethylene to a solution of compound 2 in toluene at 30° C. results in the quick consumption of the monomer and polymer formation (Example 1). Use of an additional 6 equivalents of $B(C_6F_5)_3$ increases the activity of the catalyst and decreases the polydispersity index (PDI) of the polymer (Example 2). The PDI is a measure of the distribution of molecular weights in a given polymer sample and is the weight average molecular weight divided by the number average molecular weight. It indicates the distribution of individual molecular weight number average molecular weights in a batch of polymers. The PDI has a value always greater than 1, but as the polymer chains approach uniform chain length, the PDI approaches unity.

Thermal analysis indicates the polymer has high melting point, consistent with the highly linear polymer structure (7 branches/1000 carbons) revealed by $^1$H NMR spectroscopy. The activity increases with temperature and at 75° C. (entries 3 and 4) it is comparable to those of cationic diimine nickel initiators [3]. The polymers formed at high temperature have broad PDI, more branching in the backbone (23 branches/1000 carbons) and lower melting points. No reaction occurs by using compound 1 (Example 5).

Compound 2 also initiates propylene polymerization to produce high molecular weight PP (Table 1, entries 6-8). The product is purified by precipitation from toluene using acetone. $^{13}$C NMR spectroscopy indicates the PP is isotactic rich with an mmmm pentad fraction of 0.6. In contrast, diimine nickel initiators provide atactic or syndiotactic structures [3,26]. Chain-end control by using compound 2 is suggested by the observation of mmrm sequence and absence of mmrr and mrrm sequences [27]. Signals at 36.7, and 30.2 ppm in the $^{13}$C NMR spectra reveal the presence of polyethylene segments, which were observed previously in the PP formed with cationic Ni(diimine) initiators. It has been previously proposed that 2,1 monomer insertion and subsequent chain walking to give 1,ω-enchainments results in these linear segments [1]. The PP obtained has a broad Tm at 70° C. and a Tg at −23° C.

Example 9

Example 4 can be repeated with a catalyst of formula I in which M is Pd, L' is phosphine, R' is methyl, X' is carbonyl, R is methyl, R" is ethyl, R'" is phenyl, $R^{iv}$ is hydrogen, n is 1 and L is oxygen, X" is amine, and LA is $Al(C_6F_5)_3$.

Example 10

Example 4 can be repeated with a catalyst of formula I in which M is Pt, L' is amine, R' is ethyl, X' is imine, R is ethyl, R" is propyl, R'" is hydrogen, $R^{iv}$ is hydrogen, n is 0, X" is phosphine, and LA is a proton.

Example 11

Example 4 can be repeated with a catalyst of formula I in which M is Pd, L' is ether, R' is propyl, X' is phosphine, R is ethyl, R" is propyl, R'" is n-methyl phenyl, $R^{iv}$ is methyl, n is 1 and L is amine, X" is oxygen, and LA is $BF_3$.

Example 12

Example 4 can be repeated using an olefin having formula $R^vCH=CH_2$, wherein $R^v$ is a hydrocarbyl group.

Example 13

Example 4 can be repeated using an olefin having formula $R^vCH=CH_2$, wherein $R^v$ is styrene as the olefin.

Example 14

Example 4 can be repeated using cyclopentene as the olefin.

Example 15

Example 4 can be repeated using a norbornene bearing functional group as the olefin.

In summary, we have demonstrated that a zwitterionic nickel complex supported by the 3-(2,6-diisopropylphenylimino)-but-1-en-2-olato ligand can be used to prepare high molecular weight PE and PP. The most noteworthy feature of the active site is that it is supported by an olefinic fragment, which lacks substantial steric hindrance. Such a structure departs from previous structure/reactivity relationships and theoretical predictions for cationic Ni(diimine) complexes, which require sterically demanding substituents to produce high molecular weight PE. Bonding from an olefin is considerably different from that of a nitrogen donor in that on-back bonding is a possibility. Whether this electronic feature is responsible for the increasing the ratio of the rate of chain propagation, relative to chain transfer or termination rates is unknown at this stage and requires theoretical analysis for elucidation.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

REFERENCES

1. Ittel, S. D.; Johnson, L. K.; Brookhart, M. *Chem. Rev.* 2000, 100, 1169-1203.
2. Gibson, V. C.; Spitzmesser, S. K. *Chem. Rev.* 2003, 103, 283-315
3. Johnson, L. K.; Killian, C. M.; Brookhart, M. *J. Am. Chem. Soc.* 1995, 117, 6414-6415.
4. Klabunde, U.; Ittel, S. D. *J. Mol. Catal.* 1987, 41, 123-124.
5. Ostoja-Starzewski, K. A.; Witte, J.; Reichert, K. H.; Vasiliou, G. In *Transition Metals and Organometallics as Catalysts for Olefin Polymerization*; Kaminsky, W., Sinn, H., Eds.; Springer: Berlin, 1998; p 349.
6. Younkin, T. R.; Connor, E. F.; Henderson, J. I.; Friedrich, S. K.; Grubbs, R. H.; Bansleben, D. A. *Science* 2000, 287, 460-462.

7. Jenkins, J. C.; Brookhart, M. *J. Am. Chem. Soc.* 2004, 126, 5827-5842.
8. Strauch, J. W.; Erker, G.; Kehr, G.; Fröhlich, R. *Angew. Chem. Int. Ed. Engl.* 2002, 41, 2543-2546
9. Bazan, G. C.; Rodriguez, G.; Ashe III, A. J.; Al-Ahmad, S.; Müller, C. *J. Am. Chem. Soc.* 1996, 118, 2291-2292.
10. Barnhart, R. W.; Bazan, G. C.; Mourey, T. *J. Am. Chem. Soc.* 1998, 120, 1082-1083.
11. Komon, Z. J. A.; Diamond, G. M.; Leclerc, M. K.; Murphy, V.; Okazaki, M.; Bazan, G. C. *J. Am. Chem. Soc.* 2002, 122, 15280-15285.
12. Wasilke, J. C.; Obrey, S. J.; Baker, R. T.; Bazan, G. C. *Chem. Rev.* 2005, 105, 1001-1020.
13. Bonnet, M. C.; Dahan, F.; Ecke, A.; Keim, W.; Schultz, R. P.; Tkatchenko, I. *J. Chem. Soc., Chem. Commun.* 1994, 615-616.
14. Komon, Z. J. A.; Bu, X.; Bazan, G. C. *J. Am. Chem. Soc.* 2000, 122, 1830-1831.
15. Komon, Z. J. A.; Bu, X.; Bazan, G. C. *J. Am. Chem. Soc.* 2000, 122, 12379-12380.
16. Deng, L. Q.; Margl, P.; Ziegler, T. *J. Am. Chem. Soc.* 1997, 119, 1094-1100.
17. Lee, B. Y.; Bazan, G. C.; Vela, J.; Komon, Z. J. A.; Bu, X. *J. Am. Chem. Soc.* 2001, 123, 5352-5353.
18. Chen, Y.; Wu, G.; Bazan, G. C. Angew, *Chem., Int. Ed. Engl.* 2005, 44, 1108-1112.
19. Kwon, H. Y.; Lee, S. Y.; Lee, B. Y.; Shin, D. M.; Chung, Y. K. *Dalton Transactions* 2004, 921-928.
20. Shim, C. B; Kim, Y. H.; Lee, B. Y.; Shin, D. M.; Chung, Y. K. *J. Organomet. Chem.* 2003, 675, 72-76.
21. Kim, Y. H.; Kim, T. H.; Lee, B. Y.; Woodmansee, D.; Bu, X.; Bazan, G. C. *Organometallics* 2002, 21, 3082-3084.
22. Shim, C. B.; Kim, Y. H.; Lee, B. Y.; Dong, Y.; Yun. H. *Organometallics* 2003, 22, 4272-4280.
23. Lee, B. Y.; Bu, X., Bazan, G. C. *Organometallics* 2001, 20, 5425-5431.
24. Schmid, M.; Eberhardt, R.; Kukral, J.; Rieger, B. Z. *Naturfosch. B* 2002, 57, 1141-1146.
25. Carmona, E.; Paneque, M.; Poveda, M. L. *Polyhedron* 1989, 8, 285-291.
26. Pappalardo, D.; Mazzeo, M.; Antinucci, S.; Pellecchia, C. *Macromolecules* 2000, 33, 9483-9487.
27. Ewen, J. A. *J. Am. Chem. Soc.* 1984, 106, 6355-6364

The invention claimed is:

1. A zwitterionic Group VIII transition metal complex containing a 3-(arylimino)-but-1-en-2-olato ligand.
2. The metal complex of claim 1 having the formula:

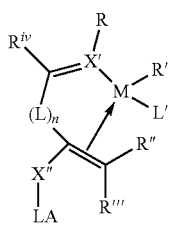

wherein M is a Group VIII transition metal;
R' is a one electron hydrocarbyl;
L' is a two electron ligand;
X' is a two electron donor N;
each R", R''', and $R^{iv}$ is independently hydrogen, an alkyl or a substituted or unsubstituted aryl group;
R is an aryl group
n is 0;
X" is oxygen
LA is a Lewis Acid; and
the olefin bearing X" is bound to the metal center.

3. The metal complex of claim 1 in which:
M is nickel;
R' is → benzyl, which represents a combination of a sigma bond and a pi-bond from the bound aromatic unit;
L' is linked to R'
X' is N;
R is an aryl group;
R" is an alkyl group;
$R^{iv}$ is an alkyl group;
R''' is hydrogen;
n is 0;
X" is oxygen; and
LA is a trisubstituted boron.
4. The metal complex of claim 3 having the formula:

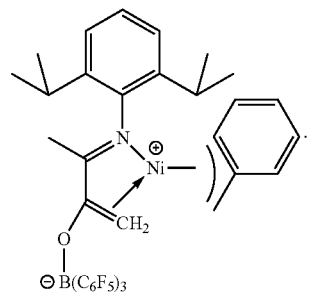

5. A process for polymerization or copolymerization of an olefin, comprising:
conducting the polymerization in the presence of a zwitterionic Group VIII transition metal complex containing a 3-(arylimino)-but-1-en-2-olato ligand.
6. The process of claim 5 in which the zwitterionic Group VIII transition metal complex has the formula:

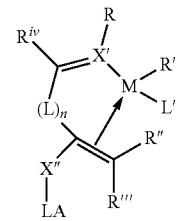

wherein M is a Group VIII transition metal;
R' is a one electron hydrocarbyl;
L' is a two electron ligand;
X' is N;
each R", R''', and $R^{iv}$ is independently hydrogen, an alkyl or a substituted or unsubstituted aryl group;
R is an aryl group
n is 0;
X" is oxygen
LA is a Lewis Acid; and
the olefin bearing X" is bound to the metal center.
7. The process of claim 6 in which:
M is nickel;
R' is → benzyl, which represents a combination of a sigma bond and a pi-bond from the bound aromatic unit;
L' is linked to R';
X' is an imine;
R is an aryl group;
R" is an alkyl group;
$R^{iv}$ is an alkyl group;
R''' is hydrogen;
n is 0;
X" is oxygen; and
LA is a trisubstituted boron.

8. The process of claim 7 in which catalyst has the formula:

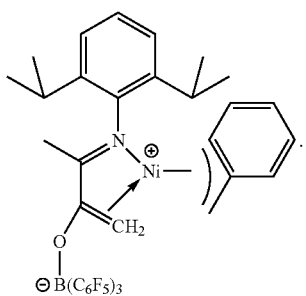

9. The process of claim 5 in which the olefin is selected from the group consisting essentially of: (1) olefins having formula $R^vCH{=}CH_2$, wherein $R^v$ is hydrogen, a substituted or unsubstituted hydrocarbyl group, or a substituted or unsubstituted hydrocarbyl bearing functional group; (2) a substituted or unsubstituted cyclopentene, (3) a substituted or unsubstituted styrene, (4) a substituted or unsubstituted norbornene derivative bearing functional group, and (5) a polar olefin.

10. The process of claim 9 in which the olefin is ethylene.

11. The process of claim 9 in which the olefin is propylene.

\* \* \* \* \*